US00PP16220P3

(12) United States Plant Patent
Challet

(10) Patent No.: US PP16,220 P3
(45) Date of Patent: Jan. 24, 2006

(54) ***CHRYSANTHEMUM* PLANT NAMED 'CHARUMBLA'**

(50) Latin Name: *Chrysanthemum morifolium*
Varietal Denomination: Charumbla

(75) Inventor: Jean-Pierre Challet, Nuaillé (FR)

(73) Assignee: Selection New Plant Sarl, Le Luc (FR)

( * ) Notice: Subject to any disclaimer, the term of this patent is extended or adjusted under 35 U.S.C. 154(b) by 56 days.

(21) Appl. No.: 10/812,937

(22) Filed: Mar. 31, 2004

(65) Prior Publication Data

US 2005/0223455 P1 Oct. 6, 2005

(51) Int. Cl.
*A01H 5/00* (2006.01)

(52) U.S. Cl. ..... Plt./288
(58) Field of Classification Search ..... Plt./288, Plt./263
See application file for complete search history.

(56) References Cited

PUBLICATIONS http://www.mobot.org/gardeninghelp/plantfinder/Plant.asp-?code=H600, Jan. 19, 2005.*

* cited by examiner

*Primary Examiner*—Anne Marie Grunberg
(74) *Attorney, Agent, or Firm*—Buchanan Ingersoll PC

(57) ABSTRACT

A new and distinct *Chrysanthemum* cultivar is provided that is a whole plant mutation of the 'Chamanda' cultivar (U.S. Plant patent application Ser. No. 10/114,954 (now abandoned), filed Apr. 4, 2002. The natural flowering time is mid-October. Attractive blossoms are formed in clusters that display white ray florets and yellow disc florets. The growth habit of the plant is rather dense, stocky, and semi-erect. Decorative medium green foliage is formed. The plant displays good culture regularity and grows well in pots.

1 Drawing Sheet

Figure 1:
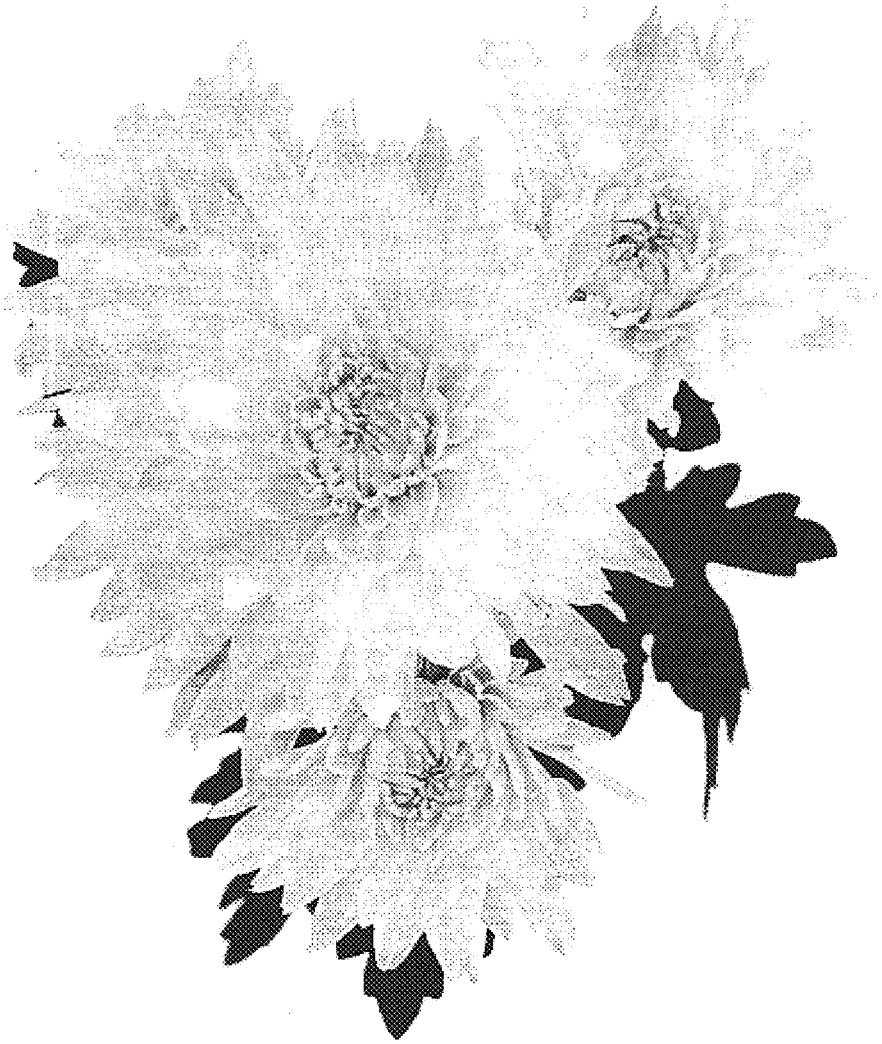

Botanical/commercial classification: *Chrysanthemum morifolium*/Decorative Pot *Chrysanthemum.*
Varietal denomination: cv. 'Charumbla'.

SUMMARY OF THE INVENTION

The present invention comprises a new and distinct cultivar of *Chrysanthemum*, botanically known as *Chrysanthemum morifolium*, and hereafter is referred to by the cultivar name 'Charumbla'.

The new cultivar was discovered during 1999 at Nuaillé, France, while present in a cultivated area where plants of the 'Chamanda' cultivar (U.S. Plant patent application Ser. No. 10/114,954, filed Apr. 4, 2002—now abandoned) were being grown. The new cultivar is believed to be a natural whole plant mutation of the 'Chamanda' cultivar of unknown causation. I was initially attracted to the new cultivar primarily because of its distinctive flower coloration. Had the new cultivar not been discovered and preserved, it would have been lost to mankind.

It was found that the new *Chrysanthemum* cultivar of the present invention displays:

(a) a rather dense, stocky, and semi-erect growth habit, (b) forms attractive flowers that display white ray florets and yellow disc florets, (c) forms decorative medium green foliage, and (d) displays good culture regularity and grows well in pots.

The new cultivar can be grown singly or in clumps in pots. It also can be grown in the landscape. The white and yellow blossoms blend nicely with the medium green foliage. Pinching is helpful to further enhance branching and produces a large number of shoots. The natural flowering time is mid-October.

Asexual reproduction of the new cultivar by the rooting of cuttings as performed at Nuaillé, France, in a controlled environment has demonstrated that the characteristics of the new cultivar are firmly fixed and are retained through successive generations of asexual propagation. The new cultivar reproduces true to type from one generation to another by such asexual reproduction.

The new cultivar can be readily distinguished from the 'Chamanda' parental cultivar. More specifically, the 'Chamanda' cultivar forms flowers of light rose and cherry red and the new cultivar forms dissimilar flowers of white and yellow.

The new cultivar also can be readily distinguished from other white-flowered *Chrysanthemum* cultivars such as 'Chasky' (U.S. Plant patent application Ser. No. 10/117,094, filed Apr. 8, 2002—now abandoned) and 'Chaclair' (U.S. Plant patent application Ser. No. 10/118,428, filed Apr. 9, 2002—now abandoned). More specifically, the 'Chasky' cultivar displays considerably smaller flowers having a diameter of approximately 3.5 to 4.5 cm which commonly include only approximately 3 to 4 rows of ray florets and disc florets that fade to white. The 'Chaclair' cultivar displays larger flowers having a diameter of approximately 9 to 11 cm which commonly include more than 25 rows of disc florets and no disc florets. The new cultivar commonly displays a flower diameter of approximately 7 to 8 cm and approximately 8 to 10 rows of ray florets. Also, the 'Chasky' and 'Chaclair' cultivars commonly display a leaf apex that is mucronate. This can be compared to a leaf apex that is acuminate for the new cultivar.

The 'Charumbla' cultivar has not been observed under all possible environmental conditions to date. Accordingly, it is possible that the phenotype may vary somewhat with variations in the environment, such as temperature, light, day length, contact with pesticides and/or subjection to grown regulation treatments.

BRIEF DESCRIPTION OF THE PHOTOGRAPH

The accompanying FIG. 1 depicts typical blossoms and foliage of a plant of 'Charumbla' cultivar while growing in a pot in a greenhouse at Nuaillé, France. The attractive white blossoms having a yellow center are illustrated.

DETAILED DESCRIPTION

The plants described were approximately three months of age and were being grown in pots in a greenhouse at Nuaillé, France. No growth regulation was used. The growing conditions approximate those commonly utilized for the commercial production of decorative pot mums. Color information is provided by reference to The R.H.S. Colour Chart of The Royal Horticultural Society, London, England.

GENERAL APPEARANCE

Rather dense, stocky and semi-erect growth habit. The plant height commonly is approximately 30 to 35 cm on average and the plant width commonly is approximately 20 to 25 cm on average. The branches commonly measure approximately 25 to 30 cm in length on average, and approximately 0.8 to 1.1 cm in diameter on average. The branch coloration commonly is near Yellow-Green Group 146A and 146B.

FOLIAGE

The leaves commonly are approximately 5 to 7 cm in length on average and approximately 2.5 to 3 cm in width on average. Each leaf possesses rough serration and commonly consists of five lobes. The inferior lobes sometimes are absent and thereby yield leaves of only three or four lobes. The leaf base commonly is asymmetrical and the leaf apex commonly is acuminate. The leaf texture is fleshy, and the sinus between the lateral lobes is rounded. There commonly are approximately 20 to 25 leaves per stem. The upper leaf surface is medium green (near Green Group 137A) and the under leaf surface is lighter and Green Group 137C in coloration. The petiole commonly is near Green Group 137C in coloration, possesses a smooth texture, is approximately 0.8 to 1.8 cm in length on average, and is approximately 0.3 to 0.5 cm in diameter on average.

FLOWERS

White blossoms with a yellow center are formed in clusters. Commonly approximately 6 to 9 flowers per stem are formed on average. The buds are rounded and commonly possess a length of approximately 0.6 to 0.8 cm on average, a diameter of approximately 0.8 to 1 cm on average and are near Green-Yellow Group 1D in coloration. The flowers possess no fragrance. The disc florets generally are erect, possess a tubular base, are approximately 0.3 to 0.5 cm in length on average, are approximately 0.1 to 0.2 cm in width on average, commonly number less than 15, and commonly are Yellow Group 4C on the upper surface and near Green-Yellow Group 1D on the under surface. The ray florets are present in approximately eight to ten rows, are incurved, possess a smooth surface texture, possess a pointed apex, are approximately 2 to 4 cm in length on average, are approximately 0.6 to 1 cm in width on average, commonly number between approximately 200 to 250 on average, and commonly are near White Group 155D in coloration on both surfaces. The flower diameter when mature commonly ranges from approximately 7 to 8 cm on average. The peduncle possesses a smooth surface texture, a length of approximately 3 to 5 cm on average, a diameter of approximately 0.3 to 0.5 cm on average, and commonly is near Green Group 141B in coloration. The receptacle possesses a flat-cupola shape, a length of approximately 0.6 to 0.8 cm on average, a diameter of approximately 0.8 to 1 cm on average, and commonly is near Green Group 141A in coloration. The reproductive parts are present among both the disc and ray florets. However, the stigma, styles, filaments, and anthers are so small and slim that it is not possible to determine their coloration and to provide additional characterization using standard evaluation techniques. No pollen or seeds have been observed.

FLOWER TIME

The natural flowering time is mid-October. The duration of the blooming is approximately three weeks. The flowers commonly last approximately 2 to 3 weeks on average on the plant and such longevity commonly is influenced by the environmental condition that are encountered. The blossoms become more white with age and may even assume a very slight pinkish hue with extreme age.

USAGE

Decorative pot mum. No particular susceptibility to diseases and pests has been observed during the growing of the new cultivar to date.

I claim:

1. A new and distinct cultivar of *Chrysanthemum* plant that displays:

(a) a rather dense, stocky, and semi-erect growth habit, (b) forms attractive flowers that display white ray florets and yellow disc florets, (c) forms decorative medium green foliage, and (d) displays good culture regularity and grows well in pots;

substantially as illustrated and described.

* * * * *